United States Patent
Bom et al.

(10) Patent No.: US 7,265,099 B1
(45) Date of Patent: *Sep. 4, 2007

(54) USE OF CHEMICAL CHELATORS AS REVERSAL AGENTS FOR DRUG-INDUCED NEUROMUSCULAR BLOCK

(75) Inventors: Antonius Helena Adolf Bom, Midlothian (GB); Alan William Muir, Lanark (GB); David Rees, Göthenburg (SE)

(73) Assignee: Organon N.V., Oss (NL)

( * ) Notice: Subject to any disclaimer, the term of this patent is extended or adjusted under 35 U.S.C. 154(b) by 0 days.

This patent is subject to a terminal disclaimer.

(21) Appl. No.: 10/049,393

(22) PCT Filed: Aug. 7, 2000

(86) PCT No.: PCT/EP00/07694

§ 371 (c)(1),
(2), (4) Date: Aug. 28, 2002

(87) PCT Pub. No.: WO01/12202

PCT Pub. Date: Feb. 22, 2001

(30) Foreign Application Priority Data

Aug. 13, 1999 (EP) .................................. 99306411

(51) Int. Cl.
 *A61K 31/724* (2006.01)
 *A61K 31/58* (2006.01)
 *A61K 31/4741* (2006.01)
 *A61K 31/225* (2006.01)

(52) U.S. Cl. ........................ 514/58; 514/176; 514/308; 514/547

(58) Field of Classification Search .................. 514/58, 514/176, 308, 547
See application file for complete search history.

(56) References Cited

U.S. PATENT DOCUMENTS

| 3,929,813 | A | 12/1975 | Higuchi et.al. | ......... 260/296 M |
| 5,180,716 | A | 1/1993 | Yaksh et al. | ................... 514/58 |
| 5,767,112 | A | 6/1998 | Poli et al. | .................. 514/172 |
| 5,834,446 | A | 11/1998 | Dow et al. | .................... 514/58 |
| 5,840,881 | A | 11/1998 | Uda et al. | ..................... 536/46 |

FOREIGN PATENT DOCUMENTS

| AU | 36628 95 A | 5/1996 |
| EP | 0 447 171 B1 | 9/1991 |
| JP | 11-246603 | 9/1999 |

OTHER PUBLICATIONS

Bom, A. et al "A novel concept of reversing neuromuscular block" Angew. Chem. Int. Ed. (2002) vol. 41, no 2, pp. 266-270.*
Adam, J. et al "Cyclodextrin-derived host molecules as reversal agents . . . " J. Med. Chem. (2002) vol. 45, pp 1806-1816.*
Tarver, G. et al "2-O-Substituted cyclodextrins as reversal agents . . . " Bioorg. Med. Chem. (2002) vol. 10, pp 1819-1827.*
Zhang, M. "Drug-specific cyclodextrins . . . " Drugs of the Future (2003) vol. 28, no 4, pp 347-354.*
Lee, C. "Structure, conformation, and action of neuromuscular blocking drugs" Brit. J. Anesth. (2001) vol. 87, no 5, pp 755-769.*
B Desire: "Inactivation of sarin and soman by cyclodextrins in vitro" EXPERIENTIA, vol. 43, No. 4, 1987, pp. 395-397.
B. Desire: "Interaction of soman with beta-cyclodextrin" Fundamental and Applied Toxicology, vol. 7, No. 4, 1986, pp. 647-657.
C. May: "Development of a toxin-bindng agent as a treatment for tunicamycinuracil toxicity: protection against tunicamycin poisoning of sheep" Australian Veterinary Journal, vol. 76, No. 11, 1998 pp. 752-756.
K. Uekama: "Effects of cyclodextrins on chlorpromazine-induced haemolysis and nervous systems responses" J. Pharm. Pharmacol., vol. 33, No. 11, 1981, pp. 707-710.
T. Irie: "Protective mechanism of beta-cyclodextrin for the hemolysis induced with phenothiazine neuroleptics in vitro" J. Pharmacobio-Dynamics, vol. 6, No. 6, 1983, pp. 408-414.
International Search Report No. PCT/EP 00/07694 dated Jul. 20, 2001.
Stella, V.J. et al. "Cyclodextrins: Their Future in Drug Formulation and Delivery," Pharmaceutical Research, vol. 14, No. 5 (1997), pp. 556-567.
Uekama, K. et al. "Cyclodextrin Drug Carrier Systems," Chem. Rev. (1998) vol. 98, pp. 2045-2076.
Khan, A. R. et al. "Methods for Selective Modifications of Cyclodextrins," Chem. Rev. (1998) vol. 98, pp. 1977-1996.
Szente, L. et al. "Highly soluble cyclodextrin derivatives: chemistry, properties, and trends in development," Advanced Drug Delivery Reviews (1999) vol. 36, pp. 17-28.
Gattuso, G. et al. "Synthetic Cyclic Oligosaccharides," Chem. Rev. (1998) vol. 98, pp. 1919-1958.
Miyake, M. et al. "Anionic Cyclophanes as Hosts for Cationic Aromatic Guests," Tetrahedron Letters, vol. 32, No. 49 (1991) pp. 7295-7298.
Miyake, M. et al. "Biomimetic Studies Using Artificial Systems. VI. [1)] Design and Synthesis of Novel Cyclophanes Having Eight Carboxyl Groups on the Aromatic Rings[2)]," Chem. Pharm. Bull., vol. 41(7) (1993) pp. 1211-1213.
Cram, D. J. et al. Macro Rings. VIII. Aromatic Substitution of the [6.6] Paracyclophane[1], J Am. Chem. Soc. (1955) vol. 77, pp. 1179-1186.

(Continued)

*Primary Examiner*—Leigh C. Maier
(74) *Attorney, Agent, or Firm*—Susan Hess

(57) ABSTRACT

The invention relates to the use of chemical chelators for the preparation of a medicament for the reversal of drug-induced neuromuscular block, to a kit for providing neuromuscular block and its reversal, and to cyclophane derivatives having general formula (A) wherein R is (a), (b) or (c); or general formula (B) wherein X is (a), (b) or (d), or a pharmaceutically acceptable salt thereof.

3 Claims, No Drawings

OTHER PUBLICATIONS

Soga, T. et al. "Modifications of Hydrophobic Cavity and their Effects on the Complex Formation with a Hydrophobic Substrate," Tetrahedron Letters, vol. 21 (1980) pp. 4351-4354.

Golden, J.H. "Bi(*anthracene*-9, 10-*dimethylene*) (*Tetrabenzo*-[2,2]-*para-cyclophane*].," J. Chem. Soc. (1961) pp. 3741-3748.

Ashton, P. R. et al. "Synthetic Cyclic Oligosaccharides—Syntheses and Structural Properties of a Cyclo[1→4)-α-L-rhamnopyranosyl-(1→4)-α-D-mannopyranosyl] trioside and -tetraoside**," Chem. Eur. J. (1996) vol. 2, No. 5, pp. 580-591.

Loukas, Y. L., "Measurement of Molecular Association in Drug: Cyclodextrin Inclusion Complexes with Improved $^1$H NMR Studies," J. Pharm. Pharmacol (1997) vol. 49, pp. 944-948.

Bisson, A. P. et al. "Cooperative Interactions in a Ternary Mixture," Chem. Eur. J. (1998) vol. 4, No. 5, pp. 845-851.

Jicsinszky, L. et al., "Cyclodextrin Derivatives," Comprehensive Supramolecular Chemistry, vol. 3, Cyclodextrins, Elsevier Science Ltd., Oxford, UK (1996) pp. 57-188.

Vogtle et al.j, "Cyclophane Hosts: Endoacidic, Endobasic, and Endolipophilic Large Cavities," Comprehensive Supramolecular Chemistry, vol. 2, Molecular recognition: Receptors for molecular guests, Atwood et al. eds; Elsevier Science Ltd., Oxford, UK (1996) pp. 211-265.

Connors, K.A. "Binding constants, The measurement of Molecular Complex Stability," Wiley-Interscience, New York (1987) pp. 24-28.

Gennaro, A. R. et al "Parental preparations," Chapter 84, Remington's Pharmaceutical Sciences, 18$^{th}$ ed., Mack Publishing Company (1990) pp. 1545-1569.

Gennaro, A. R. et al "Intravenous admixtures," Chapter 85, Remington's Pharmaceutical Sciences, 18$^{th}$ ed., Mack Publishing Company (1990) pp. 1570-1580.

Patent Abstracts of Japan Translation of JP 11-246603.

Kuroda, Y. et al., "Dynamic Molecular Motions of ρ-Methylcinnamic Acid Included into β-Cyclodextrin Derivatives: A New Type of Free-energy Relationship in Complex Formation," J. Chem. Soc. Perkin Trans. II, vol. 10 (1989) pp. 1409-1415.

Guillo, F. et al., "Synthesis of symmetrical cyclodextrin derivatives bearing multiple charges," Bull. Soc. Chim. Fr., vol. 132 (1995) pp. 857-866.

Baer, H. et al., "Heptakis [6-S-(2,3-dihydroxypropyl)-6-thio]cyclomaltoheptaose and its sulfone: water-soluble β-cyclodextrin derivatives having modified polarity," Carbohydrate Research, vol. 280 (1996) pp. 315-321.

Lindberg B. et al., "Synthesis of some 2-0-(2-hydroxyalkyl) and 2-0-(2,3-di-hydroxyalkyl) derivatives of cyclomaltoheptaose," Carbohydrate Research, NL, Elsevier Scientific Publishers B.V., Amsterdam vol. 222, No. 1 (1991) pp. 113-119.

Khan A. R. et al., "Methods for Selective Modifications of Cyclodextrins," Chemical Reviews, US, American Chemical Society, Easton, vol. 98, No. 5, (1998) pp. 1977-1996.

\* cited by examiner

USE OF CHEMICAL CHELATORS AS REVERSAL AGENTS FOR DRUG-INDUCED NEUROMUSCULAR BLOCK

FIELD OF THE INVENTION

The invention relates to the use of chemical chelators for the preparation of a medicament for the reversal of drug-induced neuromuscular block, and to a kit for providing neuromuscular block and its reversal.

BACKGROUND OF THE INVENTION

A neuromuscular blocking agent (NMBA, also called a muscle relaxant) is routinely used during the administration of anaesthesia to facilitate endotracheal intubation and to allow surgical access to body cavities, in particular the abdomen and thorax, without hindrance from voluntary or reflex muscle movement. NMBAs are also used in the care of critically-ill patients undergoing intensive therapy, to facilitate compliance with mechanical ventilation when sedation and analgesia alone have proved inadequate.

Based on their mechanisms of action, NMBAs are divided into two categories: depolarizing and non-depolarizing. Depolarizing neuromuscular blocking agents bind to nicotinic acetylcholine receptors (nAChRS) at the neuromuscular junction in a way similar to that of the endogenous neurotransmitter acetylcholine. They stimulate an initial opening of the ion channel, producing contractions known as fasciculations. However, since these drugs are broken down only relatively slowly by cholinesterase enzymes, compared to the very rapid hydrolysis of acetylcholine by acetylcholinesterases, they bind for a much longer period than acetylcholine, causing persistent depolarization of the end-plate and hence a neuromuscular block. Succinylcholine (suxamethonium) is the best known example of a depolarizing NMBA.

Non-depolarizing neuromuscular blocking agents compete with acetylcholine for binding to muscle nAChRs, but unlike depolarizing NMBAs, they do not activate the channel. They block the activation of the channel by acetylcholine and hence prevent cell membrane depolarization, and as a result, the muscle will become flaccid. Most clinically-used NMBAs belong to the non-depolarizing category. These include tubocurarine, atracurium, (cis)atracurium, mivacurium, pancuronium, vecuronium, rocuronium and rapacuronium (Org 9487).

At the end of surgery or a period of intensive care, a reversal agent of NMBAs is often given to the patient to assist the recovery of muscle function. Most commonly used reversal agents are inhibitors of acetylcholinesterase (AChE), such as neostigmine, edrophonium and pyridostigmine. Because the mechanism of action of these drugs is to increase the level of acetylcholine at the neuromuscular junction by inhibiting the breakdown of acetylcholine, they are not suitable for reversal of depolarizing NMBAs such as succinylcholine. The use of AChE inhibitors as reversal agents leads to problems with selectivity, since neurotransmission to all synapses (both somatic and autonomic) involving the neurotransmitter acetylcholine is potentiated by these agents. This non-selectivity may lead to many side-effects due to the non-selective activation of muscarinic and nicotinic acetylcholine receptors, including bradycardia, hypotension, increased salivation, nausea, vomiting, abdominal cramps, diarrhoea and bronchoconstriction. Therefore in practice, these agents can be used only after or together with the administration of atropine (or glycopyrrolate) to antagonize the muscarinic effects of acetylcholine at the muscarinic receptors in the autonomic parasympathetic neuro-effector junctions (e.g. the heart). The use of a muscarinic acetylcholine receptor (mAChR) antagonist such as atropine causes a number of side-effects, e.g., tachycardia, dry mouth, blurred vision, and furthermore may affect cardiac conduction.

A further problem with anticholinesterase agents is that residual neuro-muscular activity must be present (>10% twitch activity) to allow the rapid recovery of neuromuscular function. Occasionally, either due to hyper-sensitivity of the patient or accidental overdose, administration of NMBAs can cause complete blockade of neuromuscular function ("deep block"). At present, there is no reliable treatment to reverse such a 'deep block'. Attempts to overcome a 'deep block' with high doses of AChE inhibitors has the risk of inducing a "cholinergic crisis", resulting in a broad range of symptoms related to enhanced stimulation of nicotinic and muscarinic receptors.

There is thus a reed for an alternative method for reversing the action of NMBAs, i.e. to restore the muscular contractions.

BRIEF SUMMARY OF THE INVENTION

The present invention provides for the use of chemical chelators (or sequestrants) as reversal agents. In one aspect the invention pertains to the use of a chemical chelator capable of forming a guest-host complex for the manufacture of a medicament for the reversal of drug-induced neuromuscular block.

The use of chemical chelators as reversal agents for NMBAs has the advantage that they are effective in reversing the action of both depolarizing and non-depolarizing NMBAs, since chemical chelators do not compete with the NMBA for binding to nAChRs. Their use does not increase the level of acetylcholine and therefore they produce fewer side effects than AChE-based reversal agents. In addition, there is no need for the combined use of a AChE inhibitor and a mAChR antagonist (e.g., atropine). The chemical chelators of the invention may further be safely employed for the reversal of 'deep block'.

DETAILED DESCRIPTION OF THE INVENTION

The term chemical chelator (or sequestrant), as used in the present invention, means any organic compound which can engage in host-guest complex formation with a neuromuscular blocking agent. The chemical chelator acts as the host molecule, the neuromuscular blocking agent being the guest molecule. The specific molecular complex, the guest-host complex, is defined as an organised chemical entity resulting from the association of two or more components held together by noncovalent intermolecular forces.

The chemical chelators (or sequestrants), according to the invention, are host molecules selected from various classes of, mostly cyclic, organic compounds which are known for their ability to form inclusion complexes with various organic compounds in aqueous solution, e.g. cyclic oligosaccharides, cyclophanes, cyclic peptides, calixarenes, crown ethers and aza crown ethers. Formation of inclusion complexes (also called encapsulation, or chemical chelation) is part of the well-known area of 'supramolecular chemistry' or 'host-guest chemistry'. Many cyclic organic compounds are known to be capable of forming an inclusion complex with another molecule, organic or inorganic. The structures and chemistry of these compounds are well documented (*Comprehensive Supramolecular Chemistry*, Volumes 1–11, Atwood J. L., Davies J. E. D., MacNicol D. D., Vogtle F., eds; Elsevier Science Ltd., Oxford, UK, 1996).

Preferred chemical chelators for use with the present invention are cyclic oligosaccharides, cyclophanes and calixarenes.

Examples of cyclic oligosaccharides suitable for use with the invention are the cyclodextrins, a catagory of naturally occcurring cyclomaltooligosaccharides, the cyclomannins (5 or more α-D-mannopyranose units linked at the 1,4 positions by α linkages), the cyclogalactins (5 or more β-D-galactopyranose units linked at the 1,4 positions by β linkages), the cycloaltrins (5 or more α-D-altropyranose units linked at the 1,4 positions by α linkages), each of which are capable of forming guest-host complexes. Cyclic oligosaccharides of different monosaccharide compositions, accessible through total chemical synthesis, represent further chemical chelators capable of interaction with a neuromuscular blocking agent. For example, cyclo-[(1–4)-α-L-rhamno-pyranosyl-(1–4)-α-D-mannopyranosyl]tetraoside, was found to be effective in reversal of the action of the neuromuscular blocking agent rocuronium bromide.

A particularly preferred class of cyclic oligosaccharide chelators according to the invention is formed by the cyclodextrins:

$n = 6–9$

Cyclodextrins are cyclic molecules containing six or more α-D-glucopyranose units linked at the 1,4 positions by a linkages as in amylose. As a consequence of this cyclic arrangement, the cyclodextrins exist as conical shaped molecules with a lipophilic cavity which can attract guest molecules whilst the outside is more hydrophilic and water-soluble. Cyclodextrins composed of six, seven, eight and nine glucopyranose units are commonly known as α-, β-, γ- and δ-cyclodextrins, respectively.

Both the native cyclodextrins (α, β, γ) which are prepared by enzymatic degradation of starch, and especially a number of chemically modified forms thereof, have already found, by virtue of their ability to form guest-host complexes, numerous applications, especially in the pharmaceutical field. Stella and Rajewski (Pharmaceutical Research, 14, 556–567, 1997) have recently reviewed pharmaceutical applications of the cyclodextrins. The major applications are in the pharmaceutical formulations of drugs in order to solubilize and/or to stabilize a drug for oral, nasal, ophthalmic, dermal, rectal and parenteral administration.

The term cyclodextrin as used in relation to the present invention includes both the native cyclodextrins and chemically modified forms thereof.

An overview on such chemically modified cyclodextrins as drug carriers in drug delivery systems is described by Uekama et al. (Chemical Reviews 1998, 98, 2045–2076). Chemical modification of cyclodextrins can be made directly on the native α-, β- or γ-cyclodextrin rings by reacting a chemical reagent (nucleophiles or electrophiles) with a properly functionalised cyclo-dextrin (for an recent overview of methods for the selective modification of cyclodextrins see Khan A. R. et al. *Chem. Rev.* 1998, 98, 1977–1996). To date, more than 1,500 cyclodextrin derivatives have been made by chemical modification of native cyclodextrins (Jicsinszky L. et al *Comprehensive Supramolecular Chemistry, Volume* 3. Cyclodextrins, Atwood J. L., Davies J. E. D, MacNicol D. D., Vogtle F., eds; Elsevier Science Ltd., Oxford, UK, 1996, pp 57–188).

Many direct modifications of a native cyclodextrin result in a mixture of isomers without precisely defined positions of substitution. Such a mixture of positional isomers is often referred to as a statistic mixture, the number of substituents attached at each cyclodextrin molecule in such a statistic mixture being expressed as the average degree of substitution (DS). Most cyclodextrin derivatives studied for pharmaceutical applications are statistic mixtures (Szente L. and Szejtli J., Adv. Drug Delivery Rev. 1999, 36, 17–28). Direct modification of a cyclodextrin does not alter the constitution or the configuration of the repeating α-D-glucopyranosyl units.

Cyclodextrins can also be prepared by de novo synthesis, starting with glucopyranose (Gattuso G. et al *Chem. Rev.* 1998, 98, 1919–1958). In this way, one can prepare not only the naturally occurring cyclic (1→4)-linked cyclodextrins but also the cyclic (1→3)-, (1→2)-, and (1→6)-linked oligopyranosides. Such a synthesis can be accomplished by using various chemical reagents or biological enzymes such as cyclodextrin transglycosylase. By using different sugar units as the starting materials, one can thereby prepare various homogeneous or heterogeneous cyclic oligosaccharides. Chemical modification of cyclodextrins is thus known to modulate their properties and can be used for the design of reversal agents selective for a specific neuromuscular blocking agent.

It will be clear to the skilled person that for a particular neuromuscular blocking agent a chemical chelator host can be developed having a hydrophobic cavity of a shape and size adapted to the guest molecule, while in addition to the hydrophobic interactions between the host and the guest charge interactions can be of importance for complex formation. Since the chemical chelators of the invention are for parenteral application they will have to be water-soluble. A specific host molecule can be designed and prepared to contain functionalities complementary to those of the guest molecule in such a manner that it results in maximum intermolecular interaction via for example hydrogen-bond, hydrophobic, electrostatic, van der Waals, and π—π interactions. Thus, for example, for a guest molecule containing basic functional groups or positive charge, a host molecule containing acidic functional groups or negative charge could be made to increase ionic interaction between the guest and the host. When such a host-guest complex is formed via inclusion or partial inclusion, the cavity size of the host molecule is also very important.

The interaction between a chemical chelator and a neuromuscular blocking agent can be analyzed by physical methods such as nuclear magnetic resonance spectroscopy (nmr) and microcalorimetry.

The most preferred cyclodextrins for use in the invention are γ-cyclodextrin and derivatives thereof.

Many of the commonly used neuromuscular blocking agents, or muscle relaxants, such as rocuronium, pancuronium, vecuronium, mivacurium, atracurium, (cis)atracurium, succinylcholine and tubocurarine, are compounds having 1 or 2 cationic sites when in neutral aqueous medium. Cyclodextrins having anionic sites in their structure are among the preferred chemical chelators according to the invention.

The preference for anionic chemical chelators for the reversal of the above mentioned neuromuscular blocking agents also applies for chemical chelators of the invention which belong to the cyclophanes.

Cyclophanes are a class of bridged aromatic compounds which have well-defined hydrophobic inclusion cavities constructed by aromatic rings incorporated in their macrocyclic structures. By introducing polar and hydrophilic functional groups such as hydroxyls and carboxyls into the artificial host compounds, cyclophanes can be made water-soluble and suitable for forming inclusion complex in aqueous media (Vogtle F. et al. *Comprehensive Supramolecular Chemistry*, Volume 2. Molecular recognition: Receptors for molecular guests, Atwood, J. L., Davies, J. E. D., MacNicol, D. D., Vogtle, F., eds; Elsevier Science Ltd., Oxford, UK, 1996, pp 211–266). Water soluble anionic cyclophanes are described by Miyake et al. (Tetr. Letters 32, 7295–7298, 1991; Chem. Pharm. Bull. 41, 1211–1213, 1993) as hosts for cationic aromatic guests. Analogously, cationic cyclophanes were shown to form inclusion complexes in aqueous solution with anionic and neutral aromatic compounds.

In a preferred embodiment of the invention the chemical chelator is chosen from cyclophanes having the general formula A

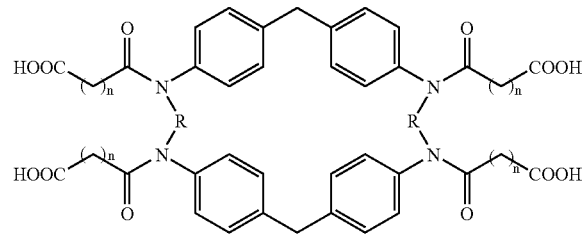

wherein R is

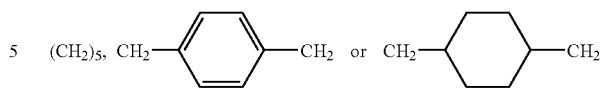

and n is 1–5; or the general formula B

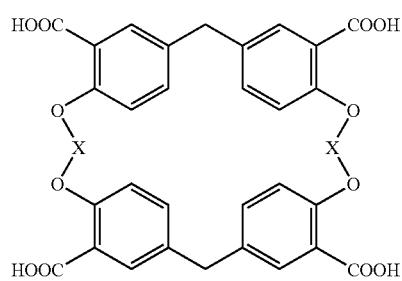

wherein X is

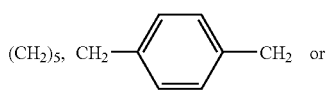

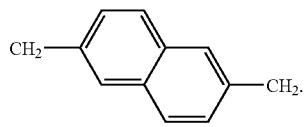

The compound according to formula A, wherein R is $CH_2$-phenyl-$CH_2$ and n is 2, i.e. N, N',N", N'''-tetrakis (3-carboxypropionyl)-3,4,5,6,7,8,26,27,28,-29,30,31-dodecahydro-1,10,24,33-tetraaza[2.2.10.2.2.1]paracyclophane (compound 23), and the compound according to formula B wherein X is $CH_2$-phenyl-$CH_2$, i.e. 1,10,24,33-tetraoxa-12,20,35,43-tetracarboxy-[2.2.1.2.2.1]-paracyclophane (compound 18) is a preferred cyclophane derivative to reverse the action of rocuronium bromide.

In a further aspect the invention provides for novel paracyclophane derivatives having formula A or Formula B, as defined above, or pharmaceutically acceptable salts thereof. Examples of such salts are the potassium, sodium and ammonium salts and the like.

The chemical chelators for use in the invention are administered parenterally. The injection route can be intravenous, subcutaneous, intradermal, intramuscular, or intraarterial. The intravenous route is the preferred one. The exact dose to be used will neccessarily be dependent upon the needs of the individual subject to whom the medicament is being administered, the degree of muscular activity to be restored and the judgement of the anaesthetist/critical-care specialist. Extracorporal application of the chemical chelators of the invention, for instance by mixing of the chemical chelator with the blood during dialysis or during plasmapheresis, is also contemplated.

In a further aspect the invention relates to a kit for providing neuromuscular block and its reversal comprising (a) a neuromuscular blocking agent, and (b) a chemical chelator capable of forming a guest-host complex with the neuromuscular blocking agent. With a kit according to the invention is meant a formulation, which contains separate pharmaceutical preparations, i.e. the neuromuscular blocking agent and a chemical chelator, i.e. the reversal agent. The components of such a kit of parts are to be used sequentially, i.e. the neuromuscular blocking agent is administered to a subject in need thereof, which is followed, at a point in time when restoration of muscle function is required, by the administration of the reversal agent, i.e. a chemical chelator capable of forming a guest-host complex with the neuromuscular blocking agent.

A preferred kit, according to the invention, contains a chemical chelator selected from the group consisting of a cyclic oligosaccharide and a cyclophane, and a neuromuscular blocking agent which is selected from the group consisting of rocuronium, vecuronium, pancuronium, rapacuronium, mivacurium, atracurium, (cis)atracurium, tubocurarine and suxamethonium. A particularly preferred kit of the invention comprises rocuronium, as the neuromuscular blocking agent, and γ-cyclodextrin, or a derivative thereof, as the chemical chelator.

Mixed with pharmaceutically suitable auxiliaries and pharmaceutically suitable liquids, e.g. as described in the standard reference, Gennaro et at., Remington's Pharmaceutical Sciences, (18th ed., Mack Publishing Company, 1990, Part 8: Pharmaceutical Preparations and Their Manufacture; see especially Chapter 84 on "Parenteral preparations", pp. 1545–1569; and Chapter 85 on "Intravenous admixtures", pp. 1570–1580) the chemical chelators can be applied in the form of a solution, e.g. for use as an injection preparation.

Alternatively, the pharmaceutical composition may be presented in unit-dose or multi-dose containers, for example sealed vials and ampoules, and may be stored in a freeze dried (lyophilised) condition requiring only the addition of the sterile liquid carrier, for example, water prior to use.

The invention further includes a pharmaceutical formulation, as hereinbefore described, in combination with packaging material suitable for said composition, said packaging material including instructions for the use of the composition for the use as hereinbefore described.

The invention is illustrated in the following examples.

EXAMPLE 1

Cyclodextrin Derivatives

Some of the cyclodextrin derivatives that were employed to demonstrate their activity as reversal agents according to the invention were commercially available:

| | Commercial Source |
|---|---|
| Compound 1: α-cyclodextrin (α-CD) | Wacker-Chemie GmbH, Munich, Germany; or ALDRICH |
| Compound 2: carboxymethyl-β-CD (DS = 3.5) sodium salt | Wacker-Chemie GmbH, Munich, Germany |

-continued

| | Commercial Source |
|---|---|
| Compound 3: 2-hydroxy-3-trimethylammonio propyl-β-CD (DS = 3.5) | Wacker-Chemie GmbH, Munich, Germany |
| Compound 4: per 2,6-dimethyl-β-CD (DS = 12.6) | Wacker-Chemie GmbH, Munich, Germany |
| Compound 5: β-cyclodextrin-phosphate sodium salt (DS = 3) | CycloLab, Ltd. Budapest, Hungary |
| Compound 6: β-cyclodextrin-phosphate sodium salt (DS = 8) | CycloLab, Ltd. Budapest, Hungary |
| Compound 7: carboxymethyl-β-CD (DS 3–3.5) | CycloLab, Ltd. Budapest, Hungary |
| Compound 8: carboxyethyl-β-CD (DS = 3) | CycloLab, Ltd. Budapest, Hungary |
| Compound 9: β-cyclodextrin (β-CD) | Wacker-Chemie GmbH, Munich, Germany; or ALDRICH |
| Compound 10: 2-hydroxypropyl-β-CD | RBI, Natick, MA 01760, USA |
| Compound 11: γ-cyclodextrin-phospate sodium salt (DS = 3) | CycloLab, Ltd. Budapest, Hungary |
| Compound 12: γ-cyclodextrin-phospate sodium salt (DS = 7) | CycloLab, Ltd. Budapest, Hungary |
| Compound 13: carboxymethyl-γ-CD (DS = 3.2) | CycloLab, Ltd. Budapest, Hungary |
| Compound 14: carboxyethyl-γ-CD (DS = 3.8) | CycloLab, Ltd. Budapest, Hungary |
| Compound 15: γ-cyclodextrin (γ-CD) | Wacker-Chemie GmbH, Munich, Germany; or FLUKA |
| Compound 16: 2-hydroxypropyl-γ-CD (DS = 4) | RBI, Natick, MA 01760, USA |

DS means the degree of substitution, which is the mean number of hydroxy functions which carry the pertinent substituent.
compounds 2 and 7 are the same, be it from different suppliers.

EXAMPLE 2

Cyclophane Derivatives

Nomenclature: the term paracyclophane refers to a family of compounds in which one or more benzene rings are built into a carbocyclic ring system and in which the p-positions of the benzene rings are part of the ring system. The conventional numbering used below for paracyclophane ring systems is that described by Cram and Abell (J. Am. Chem. Soc. 1955, 77, 1179–1186).

A: Tetraaza-paracyclophanes Derivatives:

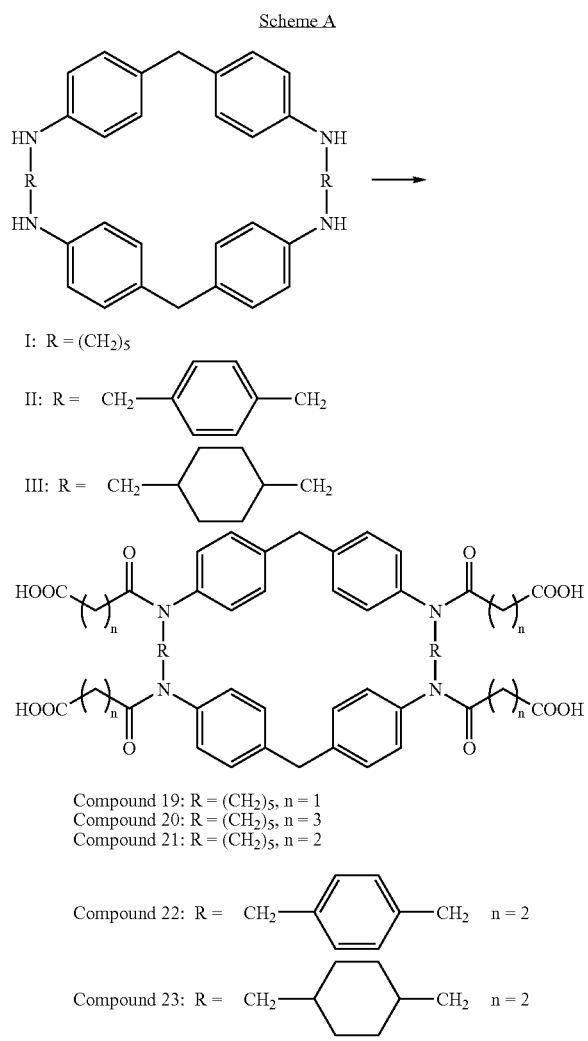

Scheme A depicts the structures of the N-(carboxy)acylated cyclophane derivatives 19–23, which were prepared by acylation of the parent cyclophanes (see Soga T. et al *Tetrahedron Lett.* 1980, 4351–4, for synthesis thereof) (1,7,21,27-tetraaza[7.1.7.1]paracyclophane (I), 1,10,24,33-tetraaza[2.2.1.2.2.1]paracyclophane (II) and 3,4,5,6,7,8,26,27,28,29,30,31-dodeca-hydydro-1,10,24,33-tetraaza[2.2.1.2.2.1]paracyclophane (III) with the appropriate activated acid derivative.

A1: Compound 21:

N, N',N", N'''-Tetrakis(3-carboxypropionyl)-1, 7, 21, 27-tetraaza[7.1.7.1]para-cyclophane To a suspension of 1,7,21,27-tetraaza[7.1.7.1]paracyclophane (400 mg, 0.75 mmol) in dichloromethane (5 ml) was added triethylamine (1.05 ml, 7.52 mmol) followed by 3-(methoxycarbonyl)propionyl chloride (0.93 ml, 7.52 mmol) dissolved in dichloromethane (3 ml). The reaction was stirred under an atmosphere of nitrogen for 12 h. The reaction was diluted with dichloromethane (20 ml) and washed with water (2×20 ml), dried (MgSO$_4$) and the solvent removed in vacuo to give a yellow oil, which was purified by chromatography on silica gel eluting with 5% methanol in dichloromethane. The resultant product crystallised on standing. The product was recystallised from chloroform/ether to give N, N',N", N'''-tetrakis[3-(methoxycarbonyl)-propionyl]-1,7, 21, 27-tetraaza[7.1.7.1]para cyclophane (480 mg, 0.48 mmol, 65%). MS (EI) m/z 989 (M+H)$^+$, $^1$H NMR (CDCl$_3$) δ 1.27 (m, 4H), 1.45 (m, 5H), 1.64 (m, 3H), 2.25 (t, J 6.8, 8H), 2.56 (t, J 6.8, 8H), 3.61 (t, J 7.6, 8H), 3.65 (s, 12H), 4.02 (s, 4H), 7.09 (d, J 8.1, 8H), 7.20 (d, J 8.1, 8H); $^{13}$C NMR (CDCl$_3$) δ 24.45, 27.85, 29.17, 29.37, 40.73, 49.47, 51.68, 128.47, 130.27, 140.15, 140.60, 171.35,173.84.

A mixture of the above tetramethylester (440 mg, 0.45 mmol), potassium hydroxide pellets (2.51 g, 45 mmol), methanol (9 ml) and water (25 ml) was heated to reflux for 4 h. The reaction was cooled to room temperature, most of the solvent removed in vacuo and the residue acidified with 2N HCl. The resultant precipitate was filtered and dried then recystallised from MeOH/H$_2$O to give the title compound 21 (142 mg, 0.15 mmol, 34%).

MS (EI) m/z 931 (M−H)—, $^1$H NMR (CD$_3$OD) δ 1.28 (m, 4H), 1.44 (m, 8H), 2.25 (m, 8H), 2.49 (m, 8H), 3.60 (m, 8H), 4.05 (s, 4H), 7.16 (d, J 7.72, 8H), 7.30 (d, J 7.72, 8H), $^{13}$C NMR (CDCl$_3$) δ 23.95, 27.44, 28.94, 29.11, 39.86, 48.62, 128.21, 129.73, 140.01, 140.35, 170.01, I. R. (KBr) 1736, 1656 cm$^{-1}$.

In a similar manner were prepared:

A2: N, N', N", N'''-Tetrakis(carboxyacetyl)-1, 7, 21, 27-tetraaza[7.1.7.1] paracyclophane (Compound 19) Starting from 1, 7, 21, 27-tetraaza[7.1.7.1]paracyclophane and methyl malonyl chloride MS (EI) m/z 877 (M+H)$^+$, $^1$H NMR (DMSO) δ 1.21 (m, 4H), 1.36 (m, 8H), 2.97 (m, 8H), 3.53 (m, 8H), 3.99 (s, 4H), 7.15 (d, J 7.95, 8H), 7.27 (d, J 7.95, 8H), 12.40 (s, 4H), $^{13}$C NMR (DMSO) δ 23.79, 27.19, 39.39, 41.44, 48.59, 128.04, 129.83, 145.05,141.02,165.69,169.23, I. R. (KBr) 1736, 1625 cm$^{-1}$.

A3: N, N', N", N'''-Tetrakis(4-carboxybutyryl)-1, 7, 21, 27-tetraaza[7.1.7.1] paracyclophane (Compound 20) Starting from 1,7,21,27-tetraaza[7.1.7.1]paracyclophane and methyl 4-(chloroformyl)butyrate MS (EI) m/z 989 (M+H)$^+$, $^1$H NMR (CD$_3$OD) δ 1.28 (m, 4H), 1.44 (m, 8H), 1.76 (m, 8H), 2.07 (t, J 7.5, 8H), 2.19 (t, J 7.5, 8H), 3.62 (m, 8H), 4.05 (s, 4H), 7.11 (d, J 8.17, 8H), 7.27 (d, J 8.17, 8H), $^{13}$C NMR (CDCl$_3$) δ 21.86, 25.54, 28.72, 34.02, 34.41, 41.70, 50.60, 129.50, 131.47, 141.82, 142.55, 174.69, 177.69, I. R. (KBr) 1736,1656 cm$^{-1}$.

A4: N, N', N", N'''-Tetrakis(3-carboxypropionyl)1, 10,24,33-tetraaza-[2.2.1.2.2.1]paracyclophane (Compound 22) Starting from cyclophane II and 3-(methoxycarbonyl)propionyl chloride $^1$H NMR (DMSO) δ 2.22 (m, 8H), 2.42 (m, 8H), 3.93 (s, 4H), 4.75 (s, 8H), 6.96 (d, J 8.27, 8H), 7.00 (s, 8H), 7.16 (d, J 8.27, 8H), 11.90 (bs, 1H), $^{13}$C NMR (DMSO) δ 28.83, 29.10, 39.93, 51.51, 125.32, 127.83, 128.22, 129.43, 136.36, 139.88, 14.00, 170.69, 173.52, I. R. (KBr) 1727, 1650 cm$^{-1}$.

A5: N, N', N'', N'''-Tetra (3-carboxypropionyl)-3,4,5,6,7,8,26,27,28,29,30,31-dodecahydro-1,10,24,33-tetraaza[2.2.1.2.2.1]paracyclophane (Compound 23) Starting from cyclophane III and 3-(methoxycarbonyl)propionyl chloride MS (EI) m/z 1012 (M−H)⁻, $^1$H NMR (DMSO) δ 0.76 (m, 8H), 1.51 (m, 4H), 1.67 (m, 8H), 2.15 (m, 8H), 2.36 (t, J 6.60, 8H), 3.37 (s, 8H), 3.97 (s, 4H), 7.19 (d, J 8.08, 8H), 7.30 (d, J 8.08, 8H), 11.86 (bs, 4H), $^{13}$C NMR (DMSO) δ 28.97, 29.09, 36.13, 52.33, 55.59, 128.09, 129.72, 141.55, 170.65, 173.52, I. R. (KBr) 1727, 1652 cm$^{-1}$.

B. Tetraoxa-paracyclophane Derivatives

The ether-linked cyclophanes (compounds 17, 18 and 25) can be synthesised by a ring construction as shown in Scheme B.

Scheme B

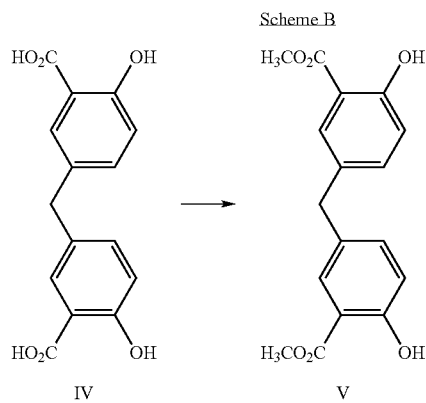

IV    V

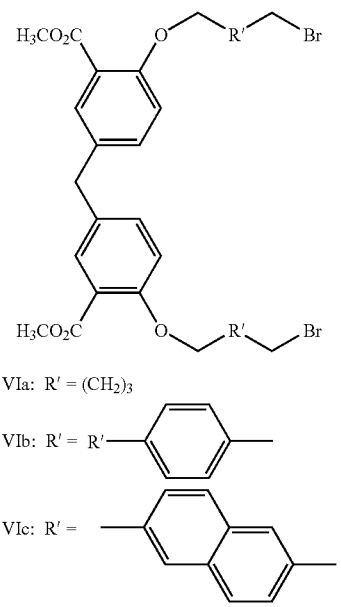

VIa: R' = (CH$_2$)$_3$

VIb: R' = R'—⟨benzene⟩—

VIc: R' = —⟨naphthalene⟩—

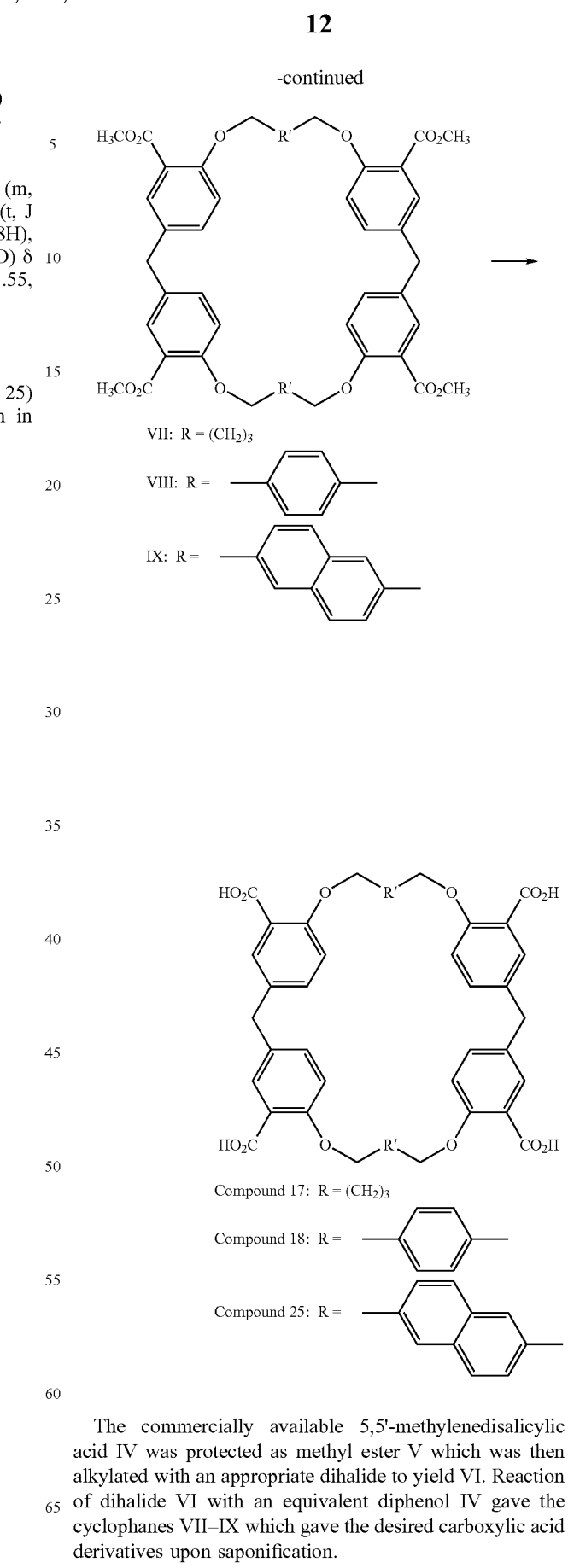

VII: R = (CH$_2$)$_3$

VIII: R = —⟨benzene⟩—

IX: R = —⟨naphthalene⟩—

Compound 17: R = (CH$_2$)$_3$

Compound 18: R = —⟨benzene⟩—

Compound 25: R = —⟨naphthalene⟩—

The commercially available 5,5'-methylenedisalicylic acid IV was protected as methyl ester V which was then alkylated with an appropriate dihalide to yield VI. Reaction of dihalide VI with an equivalent diphenol IV gave the cyclophanes VII–IX which gave the desired carboxylic acid derivatives upon saponification.

B1: Compound 17:1,7,21,27-tetraoxa-9,17,29,37-tetracarboxy[7.1.7.1]paracyclophane 3,3'-Dimethoxycarbonyl-4,4'-dihydroxydiphenyl-methane (V)

To methanol (100 ml) saturated with hydrogen chloride gas was added 3,3'-dicarboxy-4,4'-dihydroxydiphenyl-methane (10 g, 34.69 mmol) portionwise over 30 min. The mixture was then heated to reflux for 3 h, cooled to room temperature and re-saturated with hydrogen chloride gas. After a further 8 h heating at reflux the solvent was removed in vacuo and the product purified by chromatography on silica gel eluting with 25% ethyl acetate/petroleum ether to give the title compound (2.40 g, 7.59 mmol, 22%).

$^1$H NMR (CDCl$_3$) δ 3.84 (s, 2H), 3.92 (s, 6H), 6.90 (d, J 8.0, 2H), 7.25 (dd, J 8.0, 1.0, 2H), 7.63 (d, J 1.0, 2H), 10.65 (s, 2H).

4,4'-Bis(5-bromopentoxy)-3,3'-dicarboxymethyl-4,4'-dihydroxydiphenyl-methane (VIa)

To a stirred suspension of 1,4-dibromopentane (21.8 g, 94.9 mmol) and K$_2$CO$_3$ (13.1 g, 94.9 mmol) in dry dimethylformamide (380 ml) at 60° C., under an atmosphere of nitrogen, was added dropwise a solution of 3,3'-dicarboxymethyl-4,4'-dihydroxydiphenylmethane (3.0 g, 9.49 mmol) in dry dimethylformamide (190 ml). The resultant mixture was heated a further 1 h, cooled and filtered. The dimethylformamide was removed in vacuo and the product purified by chromatography eluting with 1% methanol in dichloromethane followed by a second purification eluting with 10% ethyl acetate/heptane to give the title compound (3.51 g, 5.73 mmol, 60%).

$^1$H NMR (CDCL$_3$) δ 1.60–2.02 (m, 12H), 3.44 (t, J 7.0, 4H), 3.87 (s, 8H), 4.01 (t, J 6.5, 4H), 6.87 (d, J 8.0, 2H), 7.22 (dd, J 8.0, 1.0, 2H), 7.60 (d, J 1.0, 2H).

1,7,21,27-tetraoxa-9,17,29,37-tetra(methoxycarbonyl)[7.1.7.1]paracyclophane (VII)

A solution of 4,4'-bis(5-bromopentoxy)3,3'-dicarboxymethyl-4,4'-dihydroxydiphenylmethane (3.51 g, 5.74 mmol) and 3,3'-dicarboxymethyl4, 4'-dihydroxydiphenylmethane (1.81 g, 5.74 mmol) in dry dimethylformamide (230 ml) was added dropwise via syringe pump to a stirred suspension of K$_2$CO$_3$ (7.92 g, 57.4 mmol) in dry dimethylformamide (340 ml) at 80° C. over a period of 3 h. After stirring a further 4.5 h at 80° C. and 12 h at room temperature the reaction mixture was filtered and the dimethylformamide removed in vacuo. The product was purified by chromatography on silica gel eluting with 1% methanol/dichloromethane to give the title compound (0.47 g, 0.6 mmol, 10.5%).

NMR (CDCl$_3$) δ 1.58-1.95 (m, 12H), 3.82 (s, 16H), 4.05 (t, J 8.0, 8H), 6.82 (d, J 8.0, 4H), 7.16 (dd, J 8.0, 1.0, 4H), 7.58 (d, J 1.0, 4H).

1,7,21,27-tetraoxa-9,17,29,37-tetracarboxy[7.1.7.1]paracyclophane (17)

To a suspension of 1,7,21,27-tetraoxa-9,17,29,37-tetra(methoxycarbonyl)[7.1.7.1]paracyclophane (0.47 g, 0.612 mmol) in methanol-water (3:1, 40 ml) was added solid sodium hydroxide (0.49 g, 12.2 mmol). The resultant mixture was heated to reflux for 1 h, then tetrahydrofuran (5 ml) was added and the mixture again heated to reflux for 2 h. The solvent volume was reduced by half in vacuo and insoluble material removed by filtration. The filtrate was acidified with conc hydrochloric acid and the resultant precipitate filtered dried, and further washed with methanol-water before drying to give the title compound (160 mg, 0.22 mmol, 45%).

MS (EI) m/z 711 (M–H)—, $^1$H NMR (DMSO) δ 1.51 (m, 4H), 1.68 (m, 8H), 3.81 (s, 4H), 3.99 (t, J 5.6, 8H), 6.96 (m, 4H), 7.20 (m, 4H), 7.43 (m, 4H), 12.25 (bs, 4H), $^{13}$C NMR (DMSO) δ 21.57, 27.81, 38.72, 68.47, 113.99, 121.77, 130.28, 132.60, 133.21, 155.61, 167.27, I. R. (KBr) 1743 cm$^{-1}$.

In a similar manner were prepared

B2:1,10,24,33-tetraoxa-12,20,35,43-tetracarboxy-[2.2.1.2.2.1]paracyclophane, compound 18, starting from 3,3'-dicarboxymethyl4,4'-dihydroxydiphenyl methane and α,α'-dibromo-p-xylene MS (EI) m/z 779 (M–H)$^-$, $^1$H NMR (DMSO) δ 3.75 (s, 4H), 5.15 (s, 8H), 6.91 (d, J 8.58, 4H), 7.20 (m, 4H), 7.32 (m, 8H), 7.49 (m, 4H), 12.40 (bs, 4H), $^{13}$C NMR (DMSO) δ 68.69, 84.57, 114.52, 126.54, 129.98, 132.32, 133.81, 136.28, 154.60,167.50, I. R. (KBr) 1733 cm$^{-1}$.

B3: Compound 25 starting from 3,3'-dicarboxymethyl-4,4'-dihydroxydiphenyl methane and 2,6-(dibromomethyl)naphthalene (Golden, J. H., J. Chem. Soc. 1961,3741)

MS (EI) m/z 779 (M–H)$^-$, $^1$H NMR (DMSO) ? 3.76 (s, 4H), 5.30 (s, 8H), 6.90 (m, 4H), 7.19 (m, 4H), 7.49 (m, 8H), 7.74 (m, 4H), 7.83 (m, 4H), 12.60 (bs, 4H), $^{13}$C NMR (DMSO) ??69.21, 83.84, 114.73, 121.88, 125.25, 125.37, 127.96, 130.34, 132.04, 132.67, 133.97, 135.03, 154.91, 167.52, I. R. (KBr) 1731 cm$^{-1}$.

EXAMPLE 3

Compound 24: cyclo[(1–4)-α-L-rhamnopyranosyl-(1–4)-α-D-mannopyranosyl]-tetraoside

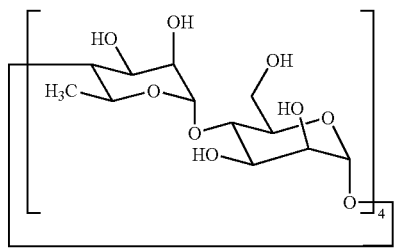

The synthesis of this cyclic octasaccharide is described by Ashton et al. in Chem. Eur. J. 1996, 2, 580–591.

EXAMPLE 4

Complexation of Rocuronium Bromide by Chemical Chelators

All the $^1$H spectra (303 K) were recorded at 400.13 MHz with 128 scans, sw=12 ppm, TD=32 k and zero filled to 64 k real points in processing. All experiments were measured at 303K.

Determination of Stoichiometry

Stock solutions of rocuronium bromide and γ-cyclodextrin (15) were prepared, both with a concentration of 6.02 mM. From these, sixteen solutions were prepared (with the mole % of rocuronium ranging from 0-100) by taking aliquots of 0–800 µl of the rocuronium bromide solution. Aliquots of the γ-cyclodextrin solution, 800–0 µl were added to make the solution a total volume of 800 µl and 100 mole % (i.e. 6.02 mM of [rocuronium bromide+γ-cyclodextrin]). $^1$H-NMR spectra were recorded as described above.

If the chemical shift change of $H_{9\alpha}$ in rocuronium bromide is defined as $\Delta\delta$ then a plot of [$\Delta\delta$*(mole % rocuronium bromide)] vs. [mole % rocuronium bromide] gives a so called Job Plot by the method of continuous variation (Connors K. A.: Binding constants, The measurement of Molecular Complex Stability; Wiley-Interscience; New York, 1987, pp 24–28). The maximum in this plot is indicative for the stoichiometry of the complex. The Job Plot for the rocuronium bromide/γ-cyclodextrin complex has a maximum at 50 mole % rocuronium, indicating that rocuronium bromide and γ-cyclodextrin form a 1:1 complex.

Determination of the Association Constants

A stock solution of rocuronium bromide: 0.821 mM in $D_2O$ was prepared. Stock solutions of β-cyclodextrin (9) and γ-cyclodextrin (15), both with concentrations of 13.1, 6.57, 1.64, and 0.411 mM in $D_2O$, were prepared. Aliquots of 50–400 µl of these solutions were then removed and made up to 400 µl with $D_2O$ (where required) and mixed with 400 µl of the rocuronium bromide solution. To extend the data range for γ-cyclodextrin (15) experiments to higher cyclodextrin concentrations three additional solutions were prepared: 16.4, 24.6, 32.8 mM in 400 µl $D_2O$. As before, these solutions were mixed with 400 µl of the rocuronium bromide solution.

$^1$H NMR spectra were recorded as descibed above.

The association constants of the complexes were derived from the plots of proton chemical shift changes of the cyclodextrin and/or rocuronium bromide signals ($\Delta\delta$) versus the mole % cyclodextrin, using a curve fitting method (Loukas Y. L., J. Pharm. Pharmacol. 1997, 49, 941; Bisson A. P., et al. Chem. Eur. J. 1998, 4, 845). The association constants are listed in Table are listed in Table A.

TABLE A

Association constants of 1:1 complex of rocuronium bromide and cyclic host compounds ($K_a$, $M^{-1}$), determined by NMR spectroscopy at 303 K.

| Chemical chelator | Association constant ($K_a$, $M^{-1}$) |
|---|---|
| β-cyclodextrin (9) | 3,100–3,900* |
| γ-cyclodextrin (15) | 10,000–20,400# |

*protons of $CH_3$-19 [rocuronium] and $H_3$ [β-cyclodextrin (9)] measured.
protons of $H_{9\alpha}$ [rocuronium] and $H_{3.5}$ [γ-cyclodextrin (15) measured.

EXAMPLE 5

Reversal of Neuromuscular Blockade In Vivo: Anaesthetized Guinea Pig

Male Dunkin-Hartley guinea pigs (bodyweight: 600–900 g) were anaesthetized by i.p. administration of 10 mg/kg pentobarbitone and 1000 mg/kg urethane. After tracheotomy, the animals were artificially ventilated using a Harvard small animal ventilator. A catheter was placed into the carotid artery for continuous monitoring of arterial blood pressure and the taking of blood samples for blood gas analysis. Heart rate was derived from the blood pressure signal. The sciatic nerve was stimulated (rectangular pulses of 0.5 ms duration at 10 s (0.1 Hz) intervals at a supramaximal voltage, using a Grass S88 Stimulator) and the force of M. gastrocnemius contractions was measured using a Grass FT03 force-displacement transducer. Contractions, blood pressure and heart rate were recorded on a multichannel Grass 7D recorder. Catheters were placed in both jugular veins. One catheter was used for the continuous infusion of a neuromuscular blocking agent. The infusion rate of the neuromuscular blocking agent was increased until a steady-state block of 85–90% was obtained. The other catheter was used for administration of increasing doses of the reversal agent. During continuous infusion of the neuromuscular blocking agent, single doses of increasing concentration of reversal agent were given. At the end of the experiment, the measured force of muscle contractions was plotted against the concentration of reversal agent, and using regression analysis techniques, the 50% reversal concentration was calculated.

Results for the reversal of the neuromuscular block, induced by the muscle relaxants rocuronium bromide (Roc), vecuronium bromide (Vec), pancuronium bromide (Pan), mivacurium chloride (Miv), atracurium besilate (Atr), cis-atracurium (Cis-Atr), tubocurarine chloride (T-C), suxamethonium chloride (Sux; succinylcholine) and rapacuronium bromide (Rap; Org 9487), by means of a series of α-, β- and γ-cyclodextrins (compounds 1–16) and modified cyclodextrins are presented in Table I. The results demonstrate that the action of each of the neuromuscular blocking agents can be reversed by intravenous administration of a cyclodextrin derivative.

TABLE I

Dose ($ED_{50}$, µmol.kg$^{-1}$) producing 50% reversal of steady-state neuromuscular block in anaesthetized guinea pigs.

| Compound* | Roc | Vec | Pan | Miv | Atr | Cis-Atr | T-C | Sux | Rap |
|---|---|---|---|---|---|---|---|---|---|
| 1: α-cyclodextrin (α-CD) | 1575 (2) | 2610 (1) | | | | | | | |
| 2: carboxymethyl-β-CD (DS = 3.5) sodium salt | 134 (2) | 800 (1) | | | | | | | |

TABLE I-continued

Dose (ED$_{50}$, μmol.kg$^{-1}$) producing 50% reversal of steady-state neuromuscular block in anaesthetized guinea pigs.

| Compound* | Roc | Vec | Pan | Miv | Atr | Cis-Atr | T-C | Sux | Rap |
|---|---|---|---|---|---|---|---|---|---|
| 3: 2-hydroxy-3-trimethylammonio propyl-β-CD (DS = 3.5) | 518 (2) | 1400 (1) | | | | | | | |
| 4: per 2,6-dimethyl-β-CD (DS = 12.6) | 70 (2) | 1313 (4) | | | | | | | |
| 5: β-cyclodextrin-phosphate sodium salt (DS = 3) | 280 (3) | | | | | | | | |
| 6: β-cyclodextrin-phosphate sodium salt (DS = 8) | 120 (2) | | | | | | | | |
| 7: carboxymethyl-β-CD (DS = 3–3.5) | 139 (3) | | | | | | | | |
| 8: carboxyethyl-β-CD (DS = 3) | 42 (3) | 103 (2) | 479 (2) | | | | | 408 (2) | 412 (2) |
| 9: β-cyclodextrin (β-CD) | 20 (3) | 636 (1) | 1050 (2) | | | | | | 358 (3) |
| 10: 2-hydroxypropyl-β-CD | 33 (3) | 1598 (4) | | | | | | | |
| 11: γ-cyclodextrin-phospate sodium salt (DS = 3) | 64 (3) | 67 (3) | 197 (2) | 292 (2) | 113 (2) | 204 (2) | 160 (2) | 160 (2) | 80 (3) |
| 12: γ-cyclodextrin-phospate sodium salt (DS = 7) | 52 (2) | | | | | | | | |
| 13: carboxymethyl-γ-CD (DS = 3.2) | 25 (4) | 30 (3) | 641 (4) | 964 (3) | 990 (2) | 893 (2) | 431 (2) | 999 (2) | 227 (2) |
| 14: carboxyethyl-γ-CD (DS = 3.8) | 7 (3) | 25 (3) | 141 (3) | 399 (2) | 421 (2) | 1558 (3) | 294 (2) | 1294 (2) | 43 (3) |
| 15: γ-cyclodextrin (γ-CD) | 4 (3) | 75 (4) | 186 (4) | 1690 (2) | 2793 (4) | 1710 (2) | 630 (2) | 1189 (2) | 57 (3) |
| 16: 2-hydroxypropyl-γ-CD (DS = 4) | 12 (3) | 123 (3) | 440 (3) | 1674 (2) | 828 (2) | 878 (2) | 909 (2) | 1340 (2) | 134 (3) |

ED$_{50}$ values are the mean of a number of experiments; the number is shown in parenthesis.

EXAMPLE 6

Reversal of Neuromuscular Block In Vitro: Isolated Mouse Hemidiaphragm Preparation Hemidiaphragms, with phrenic nerves attached, were removed from euthanized male mice (Institute of Cancer Research; bodyweight: 20–60 g). The preparations were mounted on a tissue holder and placed in a tissue bath filled with a modified Krebs-Henseleit solution (composition: 118 mM NaCl, 30 mM NaHCO3, 5 mM KCl, 1 mM KH$_2$PO$_4$, 1 mM MgSO$_4$, 30 mM glucose and 2.5 mM CaCl$_2$) at 37° C. and bubbled with 95% oxygen and 5% carbondioxide. One end of the preparation was connected with a siliconized silk suture to a Grass FT03 force-displacement transducer. An initial force of 10 mN was applied. The phrenic nerve was placed on a bipolar platinum electrode and was stimulated with rectangular pulses of 0.2 ms duration at 20 s (0.05 Hz) intervals at a supramaximal voltage, using a Grass S88 Stimulator. Contractions were recorded on a four channel Grass 79D recorder.

After the development of stable contractions, an appropriate single dose of a neuromuscular blocking agent was added to each bath to produce inhibition of contractions to approximately 5–10% of baseline values after 20 min contact time (this concentration was found to be 3.11M for rocuronium bromide). Increasing amounts of reversal agent were then administered into the bath at intervals of 10 min. The % maximum reversal was established. At the end of the experiment, the measured muscle contractions force was plotted against the concentration of reversal agent, and using regression analysis techniques, the 50% reversal concentration was calculated.

After induction of neuromuscular block by rocuronium, the % maximum reversal produced by the addition of a number of γ-cyclodextrin derivatives (compounds 11–16), a cyclic octasaccharide comprising 4 rhamnosyl-mannopyranosyl units (compound 24), or a number of paracyclophane derivatives (compounds 17–21 and 23) are presented in Table II. The results demonstrate that the neuromuscular blocking action of rocuronium can be efficiently blocked by chemical chelators of variable structure, i.e. by the γ-cyclodextrins 13, 14 and 15, by a cyclic oligosaccharide composed of rhamnose and mannose (24), and by action of the cyclophanes 18 and 23.

TABLE II

Mouse hemidiaphragm: maximum reversal (%)

| Compound | 3.1 μM rocuronium[1] |
|---|---|
| CYCLODEXTRINS | |
| 11: γ-cyclodextrin-phospate sodium salt (DS = 3) | 34 (360) |
| 12: γ-cyclodextrin-phospate sodium salt (DS = 7) | 17 (360) |
| 13: carboxymethyl-γ-CD (DS = 3.2) | 88 (180) |
| 14: carboxyethyl-γ-CD (DS = 3.8) | 87 (144) |
| 15: γ-cyclodextrin (γ-CD) | 94 (144) |
| 16: 2-hydroxypropyl-γ-CD (DS = 4) | 71 (360) |
| CYCLIC OLIGOSACCHARIDE | |
| 24: cyclo[(1–4)-α-L-rhamnopyranosyl-(1–4)-α-D-mannopyranosyl]tetraoside | 86 (288) |
| CYCLOPHANES | |
| 17: 1,7,21,27-tetraoxa-9,17,29,37-tetracarboxy-[7.1.7.1]paracyclophane | 11 (360) |
| 18: 1,10,24,33-tetraoxa-12,20,35,43-tetracarboxy--[2.2.1.2.2.1]paracyclophane | 61 (288) |
| 19: N, N', N'', N'''-tetrakis(carboxyacetyl)-1,7,21,27-tetraaza[7.1.7.1] paracyclophane | 2.4 (108) |
| 20: N, N', N'', N'''-tetrakis(4-carboxybutyryl)-1,7,21,27-tetraaza[7.1.7.1] paracyclophane | 8.7 (72) |
| 21: N, N', N'', N'''-tetrakis(3-carboxypropionyl)-1,7,21,27-tetraaza[7.1.7.1]para cyclophane | 0 (360) |
| 23: N, N', N'', N'''-tetrakis (3-carboxypropionyl)-3,4,5,6,7,8,26,27,28,29,30,31-dodecahydro 1,10,24,33-tetraaza[2.2.1.2.2.1]paracyclophane | 90 (58) |

[1]concentration of chemical chelator at maximum reversal in μM in parenthesis;

EXAMPLE 7

Calixarene Derivatives

4-Sulfonic calix[6]arene and 4-sulfonic calix[8]arene were Obtained from Aldrich Reversal of neuromuscular block in vivo, induced by rocuronium bromide, was carried out as described in Example 5. The dose ($ED_{50}$) of the calixarene derivative producing 50% reversal of steady-state neuromuscular block in the anaesthetised guinea pig was found to be 5.1 µmol/kg for the 4-sulfonic calix[6]arene and 34 µmol/kg for the 4-sulfonic calix[8]arene.

Reversal of neuromuscular block in vitro was carried out using the mouse hemidiaphragm preparation as described in Example 6. After induction of neuromuscular block (95% block) with rocuronium bromide (3.6 µM in the bath) maximum reversal of 124% and 120% were recorded for 4-sulfonic calix[8]arene and the 4-sulfonic calix[6]arene, respectively, while the 50% reversal concentrations were found to be 36 µM and 34 µM.

The invention claimed is:

1. A method for reversal of drug-induced neuromuscular block in a patient caused by a clinically-used neuromuscular blocking agent which acts by reversible binding to the acetylcholine receptor, comprising parenterally administering to said patient an effective amount of γ-cyclodextrin or a derivative thereof capable of forming a guest-host complex with the neuromuscular blocking agent inducing the neuromuscular block in the patient, and which is selected from the group consisting of rocuronium, vecuronium, pancuronium, rapacuronium, mivacurium, (cis)atracurium and tubocurarine.

2. The method according to claim 1, wherein the neuromuscular blocking agent is rocuronium or vecuronium.

3. A method for reversal of drug-induced neuromuscular block in a patient caused by a clinically-used neuromuscular blocking agent which acts by reversible binding to the acetylcholine receptor, comprising parenterally administering to said patient an effective amount of β-cyclodextrin or a derivative thereof capable of forming a guest-host complex with the neuromuscular blocking agent inducing the neuromuscular block in the patient, the neuromuscular blocking agent being rocuronium.

* * * * *